(12) United States Patent
Suval

(10) Patent No.: US 6,887,251 B1
(45) Date of Patent: May 3, 2005

(54) METHOD AND APPARATUS FOR VESSEL HARVESTING

(76) Inventor: William D. Suval, 18092 Wilka Rd. #220, Apple Valley, CA (US) 92307

( * ) Notice: Subject to any disclaimer, the term of this patent is extended or adjusted under 35 U.S.C. 154(b) by 0 days.

(21) Appl. No.: 09/905,735

(22) Filed: Jul. 12, 2001

(51) Int. Cl.⁷ ............................................... A61B 17/32
(52) U.S. Cl. ...................................................... 606/159
(58) Field of Search ................................ 606/159, 190, 606/192, 169, 170; 600/105, 210, 212

(56) References Cited

U.S. PATENT DOCUMENTS

| | | | |
|---|---|---|---|
| 5,373,840 A | * 12/1994 | Knighton | 600/106 |
| 5,695,514 A | * 12/1997 | Chin | 606/190 |
| 5,899,913 A | * 5/1999 | Fogarty et al. | 606/159 |
| 5,913,866 A | * 6/1999 | Ginn et al. | 606/174 |
| 5,928,135 A | * 7/1999 | Knight et al. | 600/104 |
| 5,928,138 A | * 7/1999 | Knight et al. | 600/201 |
| 5,938,680 A | * 8/1999 | Ginn | 606/190 |
| 5,968,066 A | * 10/1999 | Fogarty et al. | 606/190 |
| 5,970,982 A | * 10/1999 | Perkins | 128/898 |
| 6,036,713 A | * 3/2000 | Kieturakis | 606/190 |
| 6,042,538 A | * 3/2000 | Puskas | 600/114 |
| 6,059,802 A | * 5/2000 | Ginn | 606/159 |

OTHER PUBLICATIONS

The American Heritage® Dictionary of the English Language, Fourth Edition. Copyright © 2000 by Houghton Mifflin Company Definition of beveled.*

By John J. Bergan, M.D. and James S.T. Yao, M.D., Ph.D. "Surgery Of The Veins" 1985 by Grune & Stratton, Inc., Orlando, Florida p. 301–321.

By Dr. Leonardo Corcos "Surgical Instrument For Varicose Vein Removal" 1986 Derwent Publications Ltd., London, England (U.S. Office: McLean, VA); DE 3525917 A1; Bundesdruckerei 12.85 508 067/535 5/60.

* cited by examiner

Primary Examiner—Michael H. Thaler
(74) Attorney, Agent, or Firm—O'Melveny & Myers LLP

(57) ABSTRACT

The present invention is a method and device for harvesting a vessel. The vessel harvester comprises an internal stenting catheter with proximal and distal ends, a sheath catheter with proximal and distal ends, and a cylindrical cutting tube that is attachable to the distal end of the sheath catheter. The vessel harvester is used to harvest vesseal such as the greater and lesser saphenous veins, the basilic vein, the cephalic vein, and the radial artery.

7 Claims, 3 Drawing Sheets

METHOD AND APPARATUS FOR VESSEL HARVESTING

FIELD OF THE INVENTION

The present invention relates to an apparatus and method for harvesting vessels, especially veins, for use in bypass grafting surgical procedures.

BACKGROUND OF THE INVENTION

Atherosclerosis is a disease that affects hundreds of thousand of people each year. The disease can occur anywhere throughout the body including the lower extremities, the carotid arteries and the heart. When it affects the blood supply to the heart it is called coronary artery disease. Vascular complications produced by atherosclerosis, such as stenosis, aneurysm, rupture or occlusion oftentimes call for surgical intervention. If the disease is extensive, the affected artery or vessel is no longer reliable and is often replaced or bypassed around by a bypass graft, usually referred to as an "autograft." To this end, the involved section of the vessel is bypassed with an autograft surgically attached proximal to the lesion and at a point distal to the lesion to provide a bypass path for blood flow. In a patient who undergoes coronary artery bypass grafting (CABG) surgery, a non-critical vessel (artery or vein) is harvested from elsewhere in the body and is sewn into place in such a manner that reestablishes the flow of blood to the heart region that had lost or diminished its supply of blood because of the atherosclerotic lesion.

The saphenous vein in the leg is a vessel that is commonly harvested for use as a bypass graft in coronary artery surgery. It is also common to use the saphenous vein for bypass surgery in the lower extremity to bypass lesions in the femeral or popliteal arteries. However, typical procedures for harvesting a saphenous vein autograft are tedious, time consuming, and cause undesirable patient trauma. In one harvesting procedure, an incision is made along the leg for a length corresponding to the length of the autograft required, wherein the vein is transected and is stripped from the leg. The incision then must be sutured or stapled along its length. In some patients, the incision must be made along the entire length of the leg. The surgery required for harvesting a vessel in this manner is traumatic to the patient, increases recovery time, increases the patient's hospital confinement, and adds to the cost of the coronary artery surgery.

Another method of harvesting a saphenous vein is by use of an endoscope. In this method, a few small incisions are made on the leg over the saphenous vein. The saphenous vein is transected and ligated at its ends and the endoscope is inserted into the small incisions. While visualizing the vein with the endoscope, the entire length of the vein is harvested by slow dissection. The endoscope is advanced under the skin along the saphenous vein's length while transecting and ligating its connecting branches until the entire segment of the saphenous vein is free and is able to be removed. This method is more advantageous to the patient in that only a few small incisions are made and much less scarring occurs. However, the endoscopic harvesting of the vein is a difficult procedure and takes a substantial amount of time. The increased time in the operating room increases the cost of the procedure and increases the risk of infection and complications to the patient.

Other vessels are often used as well in bypass surgical procedures. For example, the radial arteries are often used as coronary conduits. The lesser saphenous, basilic, and cephalic veins are also used.

Accordingly, it would be highly desirable to provide a less invasive procedure for harvesting vessels, especially the saphenous vein, which avoids the need for a long incision, is easy to use, and does not require a substantial amount of time to complete.

SUMMARY OF THE INVENTION

The present invention provides a fast, uniform, and inexpensive way to harvest a vessel for bypass surgery. An embodiment of the present invention comprises an internal stenting catheter with proximal and distal ends, a sheath catheter with proximal and distal ends, and a cylindrical cutting tube that is attachable to the distal end of the sheath catheter. The stenting catheter is located within the sheath catheter and is used as a stent to straighten out the vein and to guide the cylindrical cutting tube around the vein. The sheath catheter is used to pull the cylindrical cutting tube under the skin and around the vein, cutting the side branches as it is pulled along the length of the vein and collecting the vein within the lumen of the cylindrical cutting tube.

The present invention is used in the following manner. The patient is prepared for surgery in standard manner and placed under proper anesthesia (local or general). A small skin incision is made at the distal end of the vessel. Next, a small skin incision is made at the proximal end of the vessel. Using a cut-down technique, for example the Seldinger Technique, the vessel is isolated and the vessel is ligated. The stenting catheter and the sheath catheter are then introduced within the vessel through the distal incision at the vessel's distal end and advanced to the vessel's proximal end where it exits the vessel and the proximal skin incision. Next, the cylindrical cutting tube is placed over the distal end of the sheath catheter and locked into place. The proximal and distal ends of the stenting catheter which are outside of the vessel and the skin are then placed into clamping devices and tension is placed on the stenting catheter until the catheter is straight. The cylindrical cutting tube is then advanced through the proximal skin incision and around the proximal end of the vessel to be harvested. The sheath catheter is used to pull the cutting tube distally down around the vessel cutting connective tissue and branches along the way. The vessel being harvested is collected within the collection lumen of the cutting tube as it is being cut free from the connective tissue and branches. Once the cutting tube has been pulled completely through the course of the vessel, the cutting tube is then removed from the distal skin incision. The cutting tube is then cut free from the stenting catheter and the remains of peel-away catheter. The harvested vessel is then removed from the lumen of the cutting tube, dilated, and the cut branches are sutured or clipped according to standard bypass grafting techniques. The vessel is now ready for the bypass grafting procedure (CABG or other bypass surgery). The area where the vessel was removed is then wrapped with elastic wraps to seal the cut edges and minimize swelling. At the end of the bypass procedure, the skin incisions are cleaned, any hematomas are expelled, and the wounds are closed.

BRIEF DESCRIPTION OF THE DRAWINGS

For a better understanding of the invention, reference is now made to the drawings where like numerals represent similar objects throughout the figures where.

DESCRIPTION OF THE PREFERRED EMBODIMENTS

Figure 1:
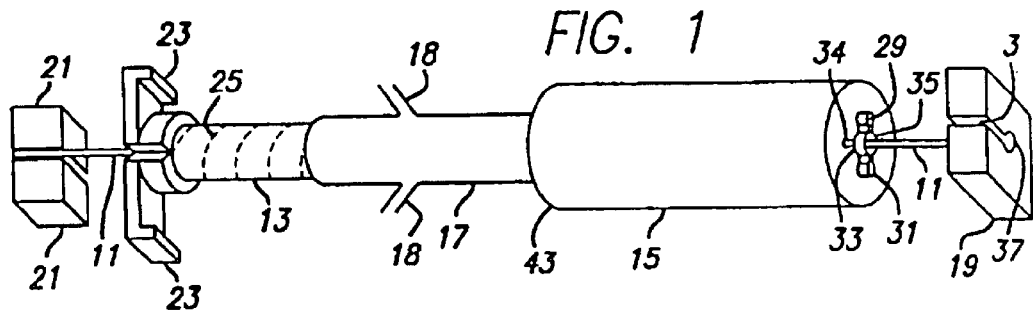
FIG. 1 is a perspective schematic view of an embodiment of the present invention for harvesting a vessel.
Figure 2:
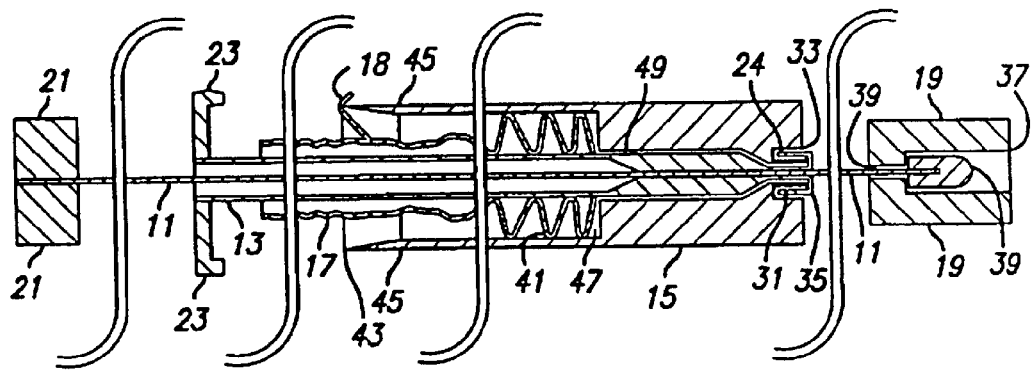
FIG. 2 is a cross-sectional view of the embodiment of FIG. 1.

Turning now to FIGS. 1 and 2, the vessel harvester of the present invention is illustrated. The vessel harvester comprises a stenting catheter 11 with proximal and distal ends, a sheath catheter 13 with proximal and distal ends, and a cylindrical cutting tube 15 with a proximal cutting edge 43 and a distal connecting port 33. The stenting catheter is located within the lumen of the sheath catheter. Both the stenting catheter and the sheath catheter are illustrated within the lumen of a vessel 17 with side branches 18. The cutting tube, on the other hand, is located around the outside of the vessel. The cutting tube is connectably attached to the distal end 35 of the sheath catheter via the connecting port and the connecting prongs 29 and 31 located on the sheath catheter.

The stenting catheter 11 can be made out of an appropriately strong biocompatible material. The catheter can be made from an extruded biocompatible plastic such as polyurethane or polyethyl terephtalate, a biocompatible metal such as surgical stainless steel wire or wire braids, a combination of wire and plastic, or other readily available materials known in the art. The catheter has to have enough flexibility to navigate the curved path of the vessel to be harvested, but also needs to have enough strength such that when axial tension is applied to straighten out the vessel, the catheter will not break. The size of the stenting catheter can vary depending on the length of the vessel to be harvested. For the greater saphenous vein, the length of the stenting catheter is about 36 to about 48 inches. For smaller veins, such as the lesser saphenous vein, the length of the stenting catheter is about 12 to about 36 inches. The diameter of the stenting catheter is about 1 to about 3 mm. The diameter has to be small enough to fit within the sheath catheter. Additionally, the catheter has to be fairly lubricious to allow for the sheath catheter to easily travel along its axial length when the vessel is being harvested. To this end the stenting catheter can be coated with a lubricious surface such as Teflon® or the like. The distal end of the stenting tube is provided with a rounded bullet nose member 39 for ease in threading the stenting catheter through the vein to be harvested. Additionally, the bullet nose can be used to fit in a clamping member 19 for placing tension on the stenting catheter once it has been threaded through the vein. The proximal end of the stenting catheter can also be placed in a clamping member 21 for opposing the tension placed by clamping member 19.

In the preferred embodiment, the sheath catheter 13 is a peel-away catheter which has two pull tabs 23 that have two notches 24 located on opposite sides for easy separation. Typical peel-away catheters have axial scoring along their length such that the catheter can peel away into two halves. It is contemplated in the present invention that this type of scoring can be used. If this type of scoring is used, then when the peel-away catheter is pulled apart, the cutting tube 15 attached to the distal end of the peel away catheter 35 is pulled straight down the stenting catheter. However, it is also contemplated in the present invention that the cutting tube is more effective when it is rotated while being pulled down. To achieve this rotation, the scoring 25 of the peel-away catheter is in a spiral configuration: Thus, when the peel-away catheter is pulled apart at its proximal end, the distal end of the peel-away catheter rotates, which in turn causes the rotation of the cutting tube. The peel away catheter can be made out of biocompatible plastics such as polyurethane, PET, or the like by extrusion and/or molding techniques or other means well known in the art. The peel-away catheter can also be reinforced with stainless steel wire to provide it strength for the rotational force needed to rotate the cutting tube within the patient. The size of the peel-away catheter can vary depending on the length of the vein to be harvested. For the greater saphenous vein, the length of the peel-away catheter is about 24 to about 48 inches. For smaller veins, such as the lesser saphenous vein, the length of the peel-away catheter is about 6 to about 36 inches. The diameter of the peel-away catheter is about 2 to about 4 mm.

Figure 3:
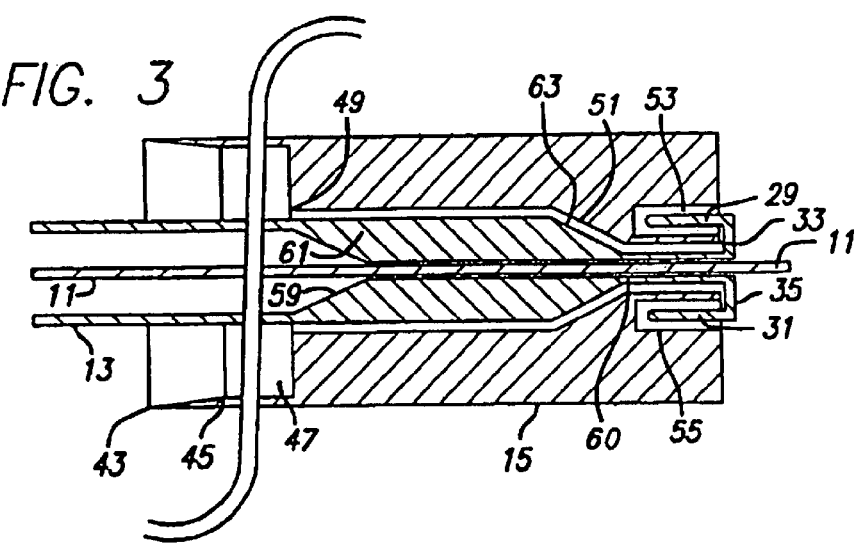
FIG. 3 is a detailed schematic view of the cutting tube of FIG. 2.

The cylindrical cutting tube 15 is a hollow tube with a vein collecting lumen 47 in the proximal portion of the tube. The proximal edge of the cutting tube is a sharp circular blade 43 which can cut connective tissue and vessel branches. The blade is created by bevel 45 which is bevelled radially outward instead of inward. This beveling configuration prevents the cutting tube from cutting the vessel to be harvest if the tube axially torques and rubs against the side of the vessel. Instead, the cutting edge acts like a razor blade traveling along the surface of the vessel and cutting the connective tissue and vessel branches. The distal end of the cutting tube has a smaller lumen 49 for closely fitting over the peel-away catheter. Turning now to FIGS. 2 and 3, the smaller lumen 49 is provided with a taper 51 near the distal end which then narrows to the distal opening 33. The distal end of the cutting tube is also provided with two connecting channels 53 and 55 that are located radially outward from the distal lumen 33. The peel-away sheath catheter 13 is provided with a taper 59 to a smaller lumen 60 for closely fitting over the stenting catheter 11. Additionally, the peel-away catheter's outer diameter through this section remains the same until the taper 63 nearer the distal end which fits within the taper 51 of the cutting tube. This provides a thick area 61 where the peel-away catheter is thicker and stiffer to support the cutting tube and track over the stenting catheter to help prevent axial torqueing of the cutting tube while it is pulled down along the vessel. The peel-away catheter is also provided with connecting prongs 29 and 31 for insertion into the connecting ports 53 and 55 of the cutting tube. The connecting prongs of the sheath catheter are passed through a channel 34 in the cutting tube (see FIG. 1) and then rotated 90 degrees for insertion into the connecting ports. Once the connecting prongs are inserted into the connecting channels, pulling apart the peel-away catheter allows for the pulling of the cutting tube down the vessel and the rotation of the cutting tube if a spiral scoring of the peel-away catheter is used.

The cutting tube can come in different sizes depending on the size and length of the vessel to be harvested. For the greater saphenous vein, the length of the cutting tube is about 7 to about 20 cm and the length of the vessel collecting lumen is about 5 to about 15 cm. For smaller vessels, such as the lesser saphenous vein or the radial artery, the length of the cutting tube is about 5 to about 15 cm and the length of the vessel collecting lumen is about 3 to about 10 cm. The diameter of the cutting tube can vary from about 3 to about 15 mm depending on the size of the vessel being harvested.

Figure 4:
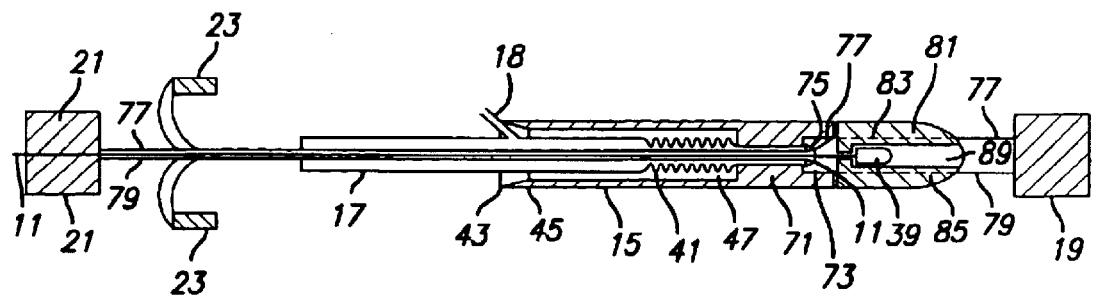
FIG. 4 is a cross-sectional view of an alternate embodiment of the present invention.

Turning now to FIG. 4 an alternate embodiment is illustrated in cross-section. In this embodiment, the sheath catheter 13 is a peel-away catheter which is longitudinally scored and has the same outer diameter until the very distal end where a beveled flange 75 is provided. The flange is inserted through a small lumen 71 of the cutting tube 15 until it rests within a larger lumen 73 of the cutting tube at its distal end. In the center of the peel away catheter is a stenting catheter 11 with a bullet nose member 39 at its distal end. Additionally, within the center of the peel away catheter are a plurality of guide wires (two being illustrated 77 and 79) for helping to keep the cutting tube aligned when it is being pulled down under the skin of the patient. The guide wires are secured at both ends of the patient in clamping member 19 and 21. The stenting catheter on the other hand is inserted into a lumen 89 in a larger bullet member 81 for actually pulling the cutting tube under the skin. The guide wires travel though the bullet member 81 in small channels 83 and 85 that help to keep the cutting tube aligned while harvesting the vein.

To harvest the vessel using the embodiment of FIG. 4, the stenting catheter is used to pull the cutting tube while the peel away catheter is used as a sheath for covering the guide wires and stenting catheter during the procedure. The vessel 17 is collected in the large lumen 47 of the cutting tube and the side branches 18 are cut with the cutting edge 43.

Figure 5:
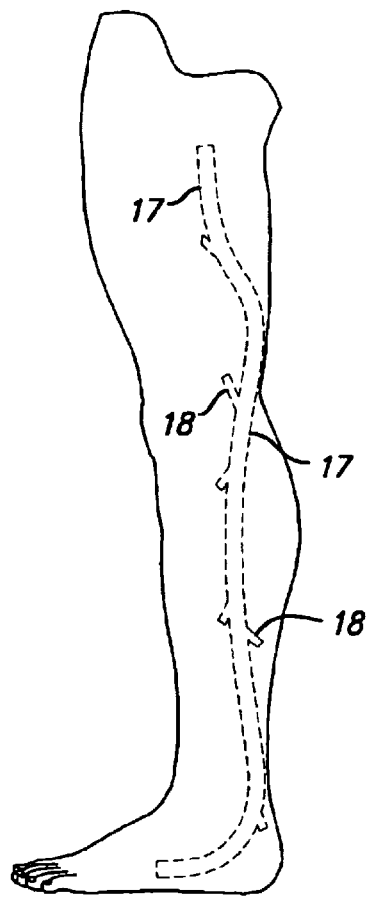
FIG. 5 is a schematic view of a lower extremity of a patient and the greater saphenous vein.
Figure 6:
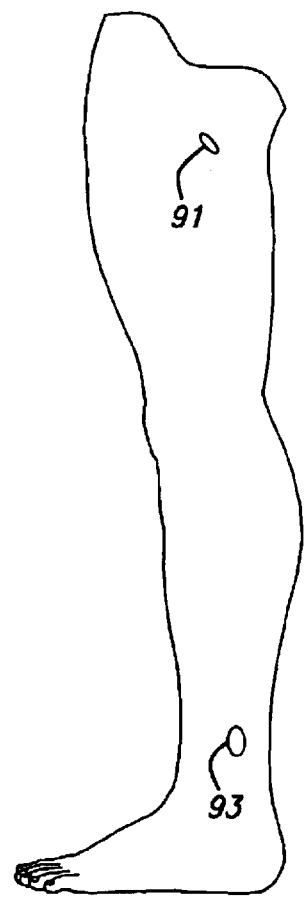
FIG. 6 is a schematic view of incisions made on the lower extremity to harvest the greater saphenous vein.

Turning now to FIGS. 5–9, the method of harvesting a vessel is illustrated. FIG. 5 schematically illustrates a greater saphenous vein 17 with side branches 18 in a leg of a patient. As can be seen, the greater saphenous vein is a curved vein located on the medial to anterior parts of the leg. Two skin incisions 91 and 93 are made along the course of the vein (see FIG. 6). As would be apparent, one skin incision is located at the distal end 93 of the vein and one is at the proximal end 91 of the vein. The location of the skin incisions can vary depending on the length of saphenous vein needed. Using a cut-down procedure such as the Seldinger technique, the saphenous vein is isolated and ligated.

Figure 7:
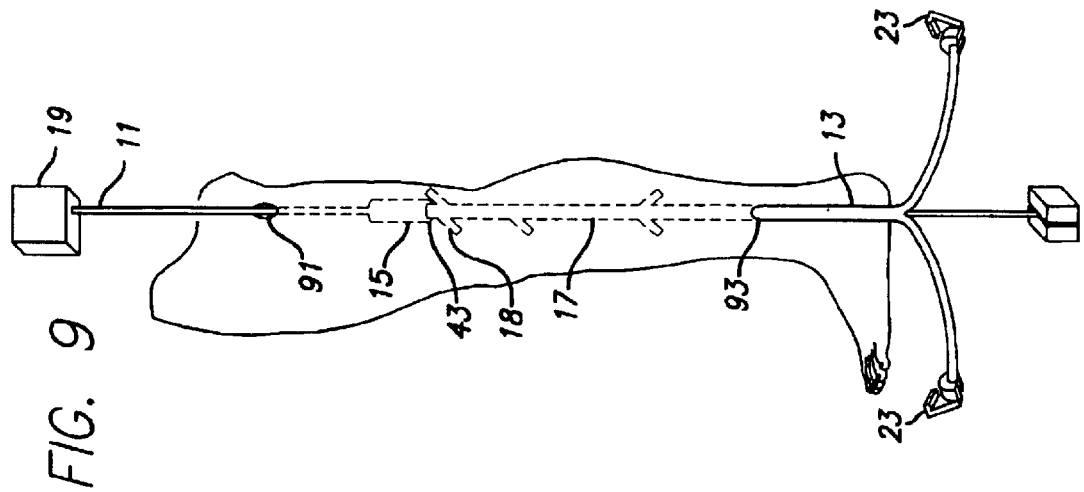
FIG. 7 is a schematic view of the stenting catheter and peel-away catheter passed through the greater saphenous vein.
Figure 8:
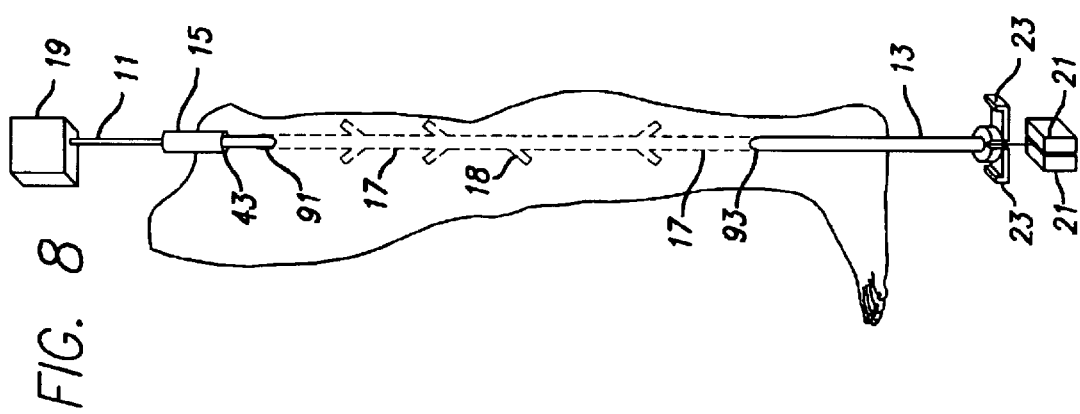
FIG. 8 is a schematic view of the stenting catheter with tension and the cutting tube connected to the distal end of the peel-away catheter.
Figure 9:
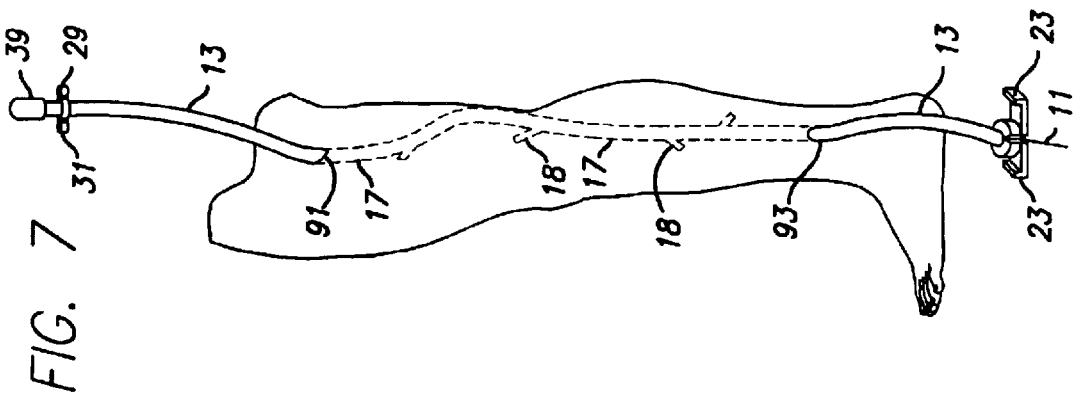
FIG. 9 is a schematic view of the peel-away catheter being pulled apart and the cutting tube advancing distally along the greater saphenous vein cutting connective tissue and side branches of the vein.

Turning now to FIG. 7, the stenting catheter 11 is then inserted into the sheath catheter 13 which is then inserted into the proximal end of the vein through incision 93 and then exits the vein at the distal incision 91 As illustrated in FIG. 8, the cutting tube is then inserted over the distal end of the peel-away catheter and locked into place using connecting tabs 29 and 31. The stenting catheter is then pulled taught and inserted into the clamping members 19 and 21. These clamping members are ideally secured to the operating table to allow for the tension to be maintained throughout the cutting process. When the stenting catheter is pulled taught, the saphenous vein 17 becomes straight. The cutting tube 15 is then inserted under the skin through the skin incision 91. The sheath catheter is a peel away catheter which is then broken apart at the tabs 23 on the proximal end and pulled apart at the serrations. While pulling the peel-away catheter apart, the cutting tube is pulled under the skin of the patient around the saphenous vein 17. As the cutting tube is being pulled, side branches 18 are cut by the cutting edge 43 of the cutting tube. If needed, the cutting tube can be manually manipulated from outside the skin of the patient to help keep it straight to prevent axial torquing and continue the harvesting of the vein. Eventually, the cutting tube is pulled all the way to the proximal incision 93 where the tube is removed from the patient. The peel-away catheter and the stenting catheter are then cut and removed from the cutting tube. The vein is then removed from the cutting tube and the cut side branches are sutured or clamped. The vein is then prepared for being a bypass conduit using standard techniques and then is used as a bypass conduit as needed.

The skin incisions 91 and 93 are then closed using standard surgical closure techniques and the leg of the patient is then wrapped with tight leg wrapping to seal the cut vein branches. The leg is monitored to insure that there is appropriate blood flow and proper recovery. If need be, hematomas are removed.

Similar methods are used for harvesting other vessels such as the lesor saphenous vein, the basilic vein, the cephalic vein, the radial artery and the like.

The vein harvesting device and method of the present invention may be embodied in other specific forms without departing from the teachings or essential characteristics of the invention. The described embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

What is claimed is:

1. A vessel harvesting device comprising a stenting catheter, a sheath catheter with proximal and distal ends, and a cutting tube that is fixedly connected to the distal end of the sheath catheter, wherein the sheath catheter is inside of the cutting tube and the cutting tube has a cutting edge facing in a proximal direction relative to the distal end of the sheath catheter, wherein the sheath catheter further comprises a peel-away catheter.

2. The vessel harvesting device of claim 1, wherein the peel-away catheter is longitudinally scored.

3. A vessel harvesting device comprising a stenting catheter, a sheath catheter with proximal and distal ends, and a cutting tube that is fixedly connected to the distal end of the sheath catheter, wherein the sheath catheter is inside of the cutting tube wherein the cuffing tube has a bevelled cutting edge that is bevelled radially outward and that faces in a proximal direction relative to the distal end of the sheath catheter.

4. A vessel harvesting device comprising a stenting catheter, a sheath catheter with proximal and distal ends, and a cutting tube that is connectable to the distal end of the sheath catheter, wherein the sheath catheter has connecting prongs at its distal end and the cutting tube has corresponding connecting ports at its distal end for connecting the cutting tube to the sheath catheter.

5. The vessel harvesting device of claim 4, wherein the cutting tube further comprises a channel for inserting the sheath catheter's connecting prongs through the lumen of the cutting tube.

6. The vessel harvesting device of claim 5, wherein the channel is located 90 degrees from the connecting ports.

7. A vessel harvesting device comprising a stenting catheter, a sheath catheter with proximal and distal ends, and a cutting tube that is connectable to the distal end of the sheath catheter, further comprising a plurality of guide wires for guiding the cutting tube during vessel harvesting.

* * * * *